United States Patent [19]
Makker et al.

[11] Patent Number: 5,942,277
[45] Date of Patent: Aug. 24, 1999

[54] IOL INSERTION APPARATUS AND METHOD FOR MAKING AND USING SAME

[75] Inventors: Harish Makker, Mission Viejo; Shih-Liang S. Yang, Laguna Hills; Daniel G. Brady, Mission Viejo; Robert E. Glick, Lake Forest, all of Calif.

[73] Assignee: Allergan, Waco, Tex.

[21] Appl. No.: 08/903,282

[22] Filed: Jul. 30, 1997

Related U.S. Application Data

[62] Division of application No. 08/676,699, Jul. 10, 1996, Pat. No. 5,716,364.

[51] Int. Cl.$^6$ ............................... B05D 7/22; B05D 3/06; B05D 3/00
[52] U.S. Cl. .......................... 427/2.28; 427/2.1; 427/230; 427/238; 427/384; 427/536; 427/539
[58] Field of Search ..................................... 427/2.28, 2.1, 427/536, 539, 491, 230, 237, 238, 384

[56] References Cited

U.S. PATENT DOCUMENTS

| | | | |
|---|---|---|---|
| 4,261,806 | 4/1981 | Asia et al. | 427/489 |
| 4,681,102 | 7/1987 | Bartell | 128/303 R |
| 4,722,906 | 2/1988 | Guire | 436/501 |
| 4,740,282 | 4/1988 | Gesser et al. | 427/585 |
| 4,767,414 | 8/1988 | Williams et al. | 604/230 |
| 4,806,382 | 2/1989 | Goldberg et al. | 427/2 |
| 4,842,889 | 6/1989 | Hu et al. | 427/536 |
| 4,844,986 | 7/1989 | Karakelle et al. | 427/2.11 |
| 4,919,130 | 4/1990 | Stoy et al. | 606/107 |
| 4,973,493 | 11/1990 | Guire | 427/2 |
| 4,979,959 | 12/1990 | Guire | 623/66 |
| 5,028,597 | 7/1991 | Kodama et al. | 514/56 |
| 5,073,166 | 12/1991 | Parks et al. | 609/93 |
| 5,084,315 | 1/1992 | Karimi et al. | 427/2.28 |
| 5,094,876 | 3/1992 | Goldberg et al. | 427/2 |
| 5,098,618 | 3/1992 | Zelez | 264/22 |
| 5,108,776 | 4/1992 | Goldberg et al. | 427/2 |
| 5,130,160 | 7/1992 | Goldberg et al. | 427/2 |
| 5,135,516 | 8/1992 | Sahatjian et al. | 604/265 |
| 5,190,552 | 3/1993 | Kelman | 606/107 |
| 5,217,492 | 6/1993 | Guire et al. | 623/11 |
| 5,258,041 | 11/1993 | Guire et al. | 623/66 |
| 5,263,992 | 11/1993 | Guire | 623/66 |
| 5,290,548 | 3/1994 | Goldberg et al. | 428/78.8 |
| 5,303,714 | 4/1994 | Abele et al. | 128/772 |
| 5,304,182 | 4/1994 | Rheinish et al. | 606/107 |
| 5,331,019 | 7/1994 | Payne, Jr. et al. | 522/75 |
| 5,331,027 | 7/1994 | Whitbourne | 524/37 |
| 5,336,263 | 8/1994 | Ersek et al. | 623/11 |
| 5,425,734 | 6/1995 | Blake | 606/107 |
| 5,429,839 | 7/1995 | Graiver et al. | 427/155 |
| 5,441,488 | 8/1995 | Shimura et al. | 604/265 |
| 5,474,562 | 12/1995 | Orchowski et al. | 606/107 |
| 5,503,631 | 4/1996 | Onishi et al. | 604/96 |
| 5,576,072 | 11/1996 | Hostettler et al. | 427/2.22 |
| 5,693,034 | 12/1997 | Buscemi et al. | 604/265 |

FOREIGN PATENT DOCUMENTS

| | | |
|---|---|---|
| 0480809 | 4/1992 | European Pat. Off. |
| 3610925 | 1/1987 | Germany |
| 7900327 | 6/1979 | WIPO |
| 9316176 | 8/1993 | WIPO |
| 9420027 | 9/1994 | WIPO |
| 9522287 | 8/1995 | WIPO |
| 9622062 | 7/1996 | WIPO |

*Primary Examiner*—Diana Dudash
*Attorney, Agent, or Firm*—Frank J. Uxa

[57] ABSTRACT

Method of making an apparatus for inserting intraocular lenses (IOLs) into eyes include a hollow tube including a material and having a plasma exposed interior wall defining a hollow space through which an IOL is passed and an outlet through which the IOL is passed from the hollow space into an eye, and a lubricity enhancing component physically secured to said hollow tube and concentrated at or near the interior wall in an amount effective to facilitate the passage of the IOL through the hollow space.

19 Claims, 2 Drawing Sheets

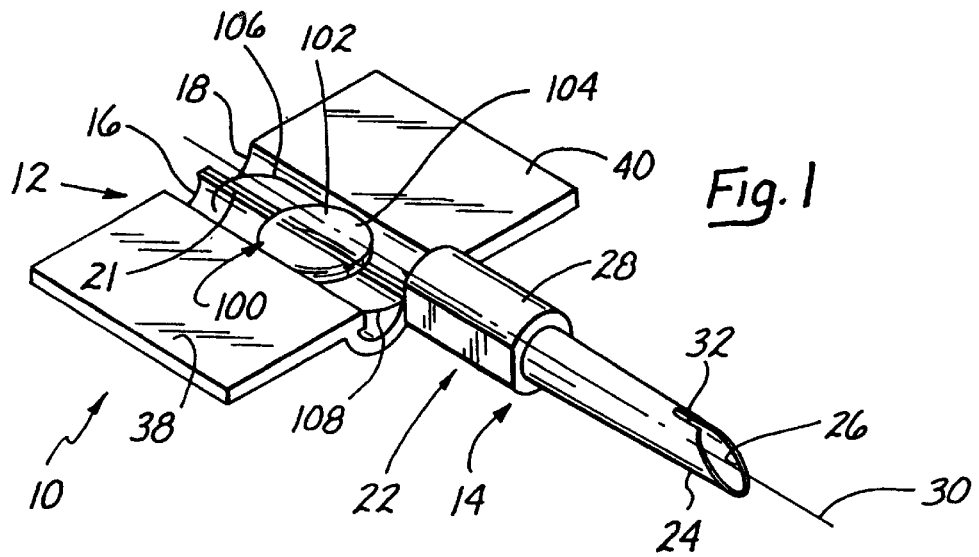
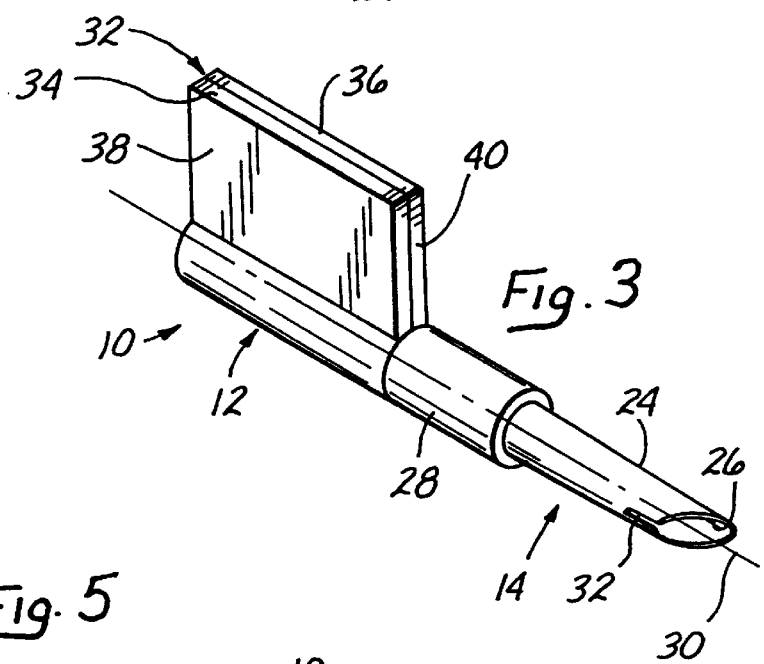
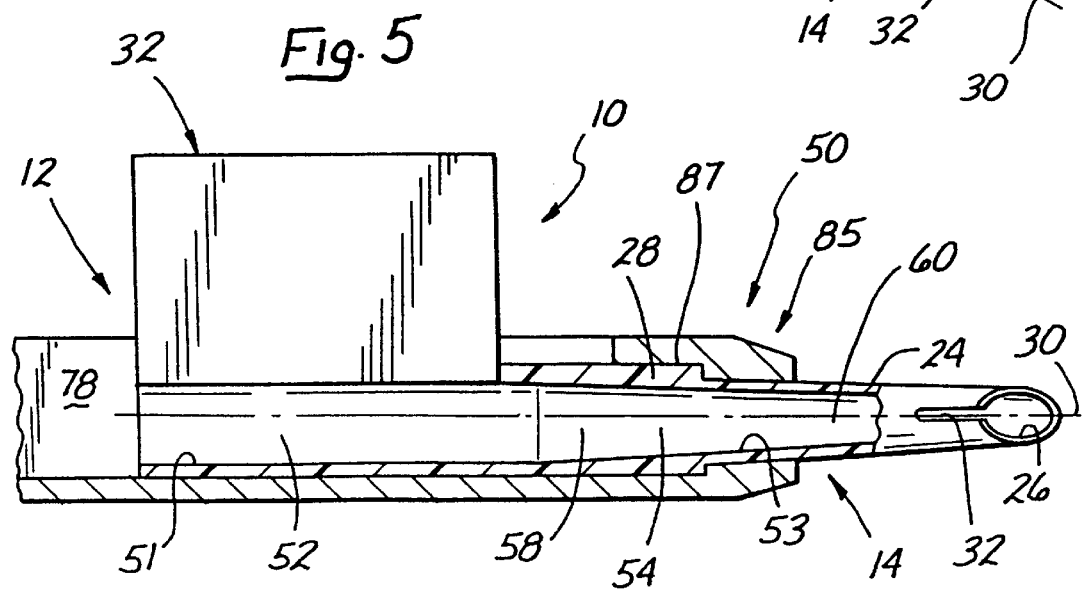

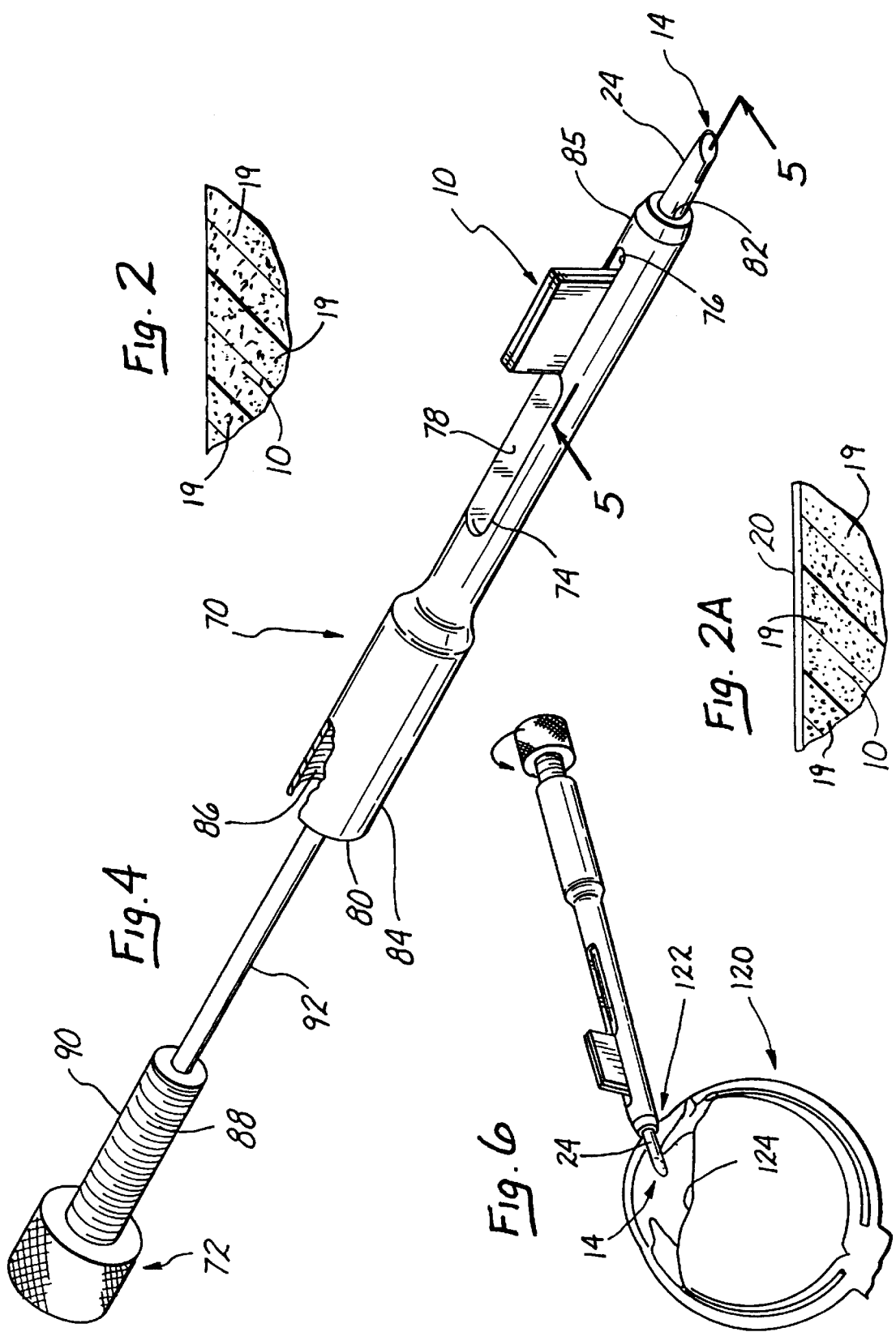

IOL INSERTION APPARATUS AND METHOD FOR MAKING AND USING SAME

This is a division of application Ser. No. 08/676,699 filed Jul. 10, 1996, now U.S. Pat. No. 5,716,364.

BACKGROUND OF THE INVENTION

The present invention relates to apparatus for inserting an intraocular lens through a small incision into an eye, to methods for making such apparatus and to methods for inserting an intraocular lens into an eye. More particularly, the invention relates to an apparatus which has enhanced lubricity and is useful for inserting a foldable intraocular lens into an eye, to methods for making such apparatus and to methods using such apparatus to insert a foldable intraocular lens into an eye.

An intraocular lens (IOL) is implanted in the eye, for example, as a replacement for the natural crystalline lens after cataract surgery or to alter the optical properties of (provide vision correction to) an eye in which the natural lens remains. IOLs often include an optic, and preferably at least one flexible fixation member or haptic which extends from the optic and becomes affixed in the eye to secure the lens in position. The optic normally includes an optically clear lens. Implantation of such IOLs into the eye involves making an incision in the eye. It is advantageous, to reduce trauma and speed healing, to have an incision size as small as possible.

IOLs are know which are foldable (deformable) so that the IOL can be inserted through a smaller incision into the eye. A substantial number of instruments have been proposed to aid in inserting such a foldable lens in the eye.

Many of the prior art IOL insertion systems load and/or fold the lens at the distal end, that is at the end closest to the eye or the end inserted into the eye. Such "distal loading" systems often disadvantageously include a space consuming loading component at or near the distal end of the system which causes the distal end to be relatively large. This relatively large distal end makes inserting the IOL through a small incision more difficult, if not impossible. Systems which fold and load the IOL proximally of the distal end provide certain advantages, such as reduced stress on the IOL and/or inserter, relative to "distal loading" systems.

However, whether using a distal loading or proximal loading system, one factor which limits the size of the inserter tube involves the inserter tube itself. For example, the material from which the inserter tube is made, for example, polypropylene and the like polymeric materials, may not be compatible or otherwise susceptible to causing optics, for example, made from silicone polymeric materials, to pass through relatively small hollow spaces. For example, the injector tubes may be made of materials, in particular polymeric materials, which have insufficient lubricity to facilitate the passage of a folded IOL through the tube.

As a result of this lack of lubricity, the hollow space of the injector tube must be made relatively larger to accommodate the folded intraocular lens. This is detriment since, as noted above, it is advantageous to have the smallest possible incision for insertion of the IOL. In addition, if one were to use a small diameter tube to pass the IOL, excessive force might be needed to pass the IOL through the small hollow space thereby increasing the risks of damaging the IOL and, in extreme cases, even damaging the eye into which the IOL is placed.

One approach that may be considered is to use a lubricity agent, for example, such as conventional visco-elastic agents, in the hollow space of the tube to facilitate passing the IOL through the insertion apparatus. However, such lubricity agents in and of themselves occupy valuable space, thereby at least partially defeating the purpose of using such agents. Also, such lubricity agents often end up in the eye, thereby creating the risk of causing trauma and/or irritation and/or damage to the eye.

It would be advantageous to provide straightforward IOL insertion apparatus and methods for using same which facilitate the passage of folded IOLs through the apparatus in a controlled manner without using excessive force.

SUMMARY OF THE INVENTION

New apparatus for injecting IOLs and methods for making and using such apparatus have been discovered. The present apparatus achieve enhanced lubricity, thus providing for the use of effective, reliable and non-excessive amounts of force to inject a folded IOL into an eye. The present IOL inserter production methods provide inserters which have very effective and reliable lubricity properties. The present invention is easy to practice. The methods of use included in the present invention often involve surgical techniques which are well practiced and conventionally used to insert IOLs into eyes.

In general, the present invention involves apparatus for inserting IOLs into an eye which include a lubricity enhancing component physically secured to the apparatus and concentrated at or near the interior wall or walls of the apparatus, for example, at or near the interior wall of the apparatus defining a hollow space through which an IOL is passed. It has been found that the inclusion of such a physically secured or bonded lubricity enhancing component is effective to facilitate the passage of the IOL through the apparatus. Physically securing or bonding such lubricity enhancing components in or on the apparatus is particularly effective since the amount of such component present, and the degree of enhanced lubricity obtained, is conveniently controlled and stable on a long term basis, for example, the apparatus has a relatively long shelf life before use. Preferably, a reduced amount of the physically secured or bonded lubricity enhancing component passes into the eye during use of the present apparatus relative to a similar or substantially identical apparatus on which the lubricity enhancing component is not bonded or secured to the apparatus.

In one embodiment, the present apparatus include an interior wall which is a plasma-exposed interior wall. This plasma-exposed interior wall preferably has an enhanced ability to physically secure or bond the lubricity enhancing component relative to a substantially identical interior wall which is not plasma-exposed. In one useful embodiment, the plasma-exposed interior wall facilitates forming the lubricity enhancing component concentrated at or near the interior wall of the hollow tube.

In general, the present methods for producing IOL insertion apparatus comprise exposing a hollow tube including a material and having an interior wall defining a hollow space through which an IOL is passed and an outlet though which the IOL is passed from the hollow space into an eye to an effective plasma, and providing an effective amount of a lubricity enhancing component at or near the interior surface. It has been found that the combination of the exposing step and the providing step is effective to facilitate the passage of the IOL through the hollow space.

The use of the present IOL insertion apparatus allows successful injection of silicone-based IOLs, for example, employing inserters made of polypropylene and the like polymeric materials, through incisions of about 3.5 mm or about 3.2 mm or less, preferably about 3.0 mm or less, and still more preferably about 2.8 mm or less.

In one broad aspect of the present invention, apparatus for inserting IOLs through small incisions into eyes are provided. Such apparatus comprise a hollow tube including (or made of) a material, preferably a polymeric material, and having an interior wall defining a hollow space through which an IOL is passed and an outlet, preferably a distal end opening, through which the IOL is passed from the hollow space into an eye. A lubricity enhancing component, preferably selected from hydrophilic components, oleophilic components and mixtures thereof, more preferably selected from oleophilic components, other than the material, is physically secured or bonded to the hollow tube and concentrated at or near the interior wall. The hollow tube, and in particular the interior wall, is preferably exposed to a plasma, more, preferably a sub-atmospheric pressure oxygen-containing plasma. The combination of the lubricity enhancing component and exposing the interior wall of the hollow tube to plasma preferably is effective to facilitate the passage of the IOL through the hollow space. The lubricity enhancing component preferably is present in a minor amount, more preferably in the range of about 0.1% to about 1% or about 10% or about 20%, of the total weight of the hollow tube. The lubricity enhancing component is physically secured, for example, physically bonded, admixed or combined, to the other material making up the hollow tube using methods known in the art, such as by blending or mixing the lubricity enhancing component and other material prior to forming the hollow tube and/or forming a coating of lubricity enhancing components on the already formed hollow tube.

By "physically" securing or bonding is meant a non-covalent chemical bonding joining or coupling, and preferably a non-chemical bonding, joining or coupling. Some interaction, for example, ionic and/or electrical interactions may occur between the lubricity enhancing component and the other material or materials making up the hollow tube. However, the present "physical" securing or bonding is clearly distinguished from forming covalent chemical bonds between the lubricity enhancing component and the other material or materials making up the hollow tube. The prior art has suggested providing covalent chemically bonded lubricants to avoid losing the lubricant during use. It has now been found that physically secured or bonded lubricity enhancing components have a reduced tendency to be lost (from the IOL inserter) during use of the present IOL inserters. Thus, physically securing or bonding the lubricity enhancing component to the hollow tube is any suitable coupling or joining which is not covalent chemical bonding of the lubricity enhancing component to the other material of the hollow tube.

In a particularly useful embodiment, the lubricity enhancing component is effective to reduce the force needed to pass the IOL through the hollow space of the tube relative to the force needed to pass an identical IOL through the hollow space of a similar apparatus without the lubricity enhancing component. This "reduced force" feature of the present invention is particularly useful, even when no reduction in the size of the incision is obtained. The use of reduced force allows the surgeon to have more control of the rate at which the IOL is inserted into the eye and, in addition, reduces the risk of damage to the eye during IOL insertion.

The material from which the hollow tube preferably is made is a polymeric material, for example, a hydrophobic polymeric material, more preferably selected from polyolefins, such as polypropylene and the like materials.

In one useful embodiment, the present apparatus further comprises a loading portion including a material and having an internal wall defining a chamber sized and adapted to receive an IOL for passage into the hollow space. A further lubricity enhancing component, preferably another amount of the same lubricity enhancing component employed in the hollow tube, preferably is physically secured to the loading portion and concentrated at or near the internal wall of the loading portion. This further lubricity enhancing component is effective to facilitate the passage of an IOL into the hollow space. The internal wall of the loading portion preferably is exposed to a further plasma, preferably the same plasma used with the hollow tube. In one embodiment, the combination of the further lubricity enhancing component and the further plasma is effective to further facilitate the passage of the IOL into the hollow space. Both the interior wall of the hollow tube and the internal wall of the loading portion preferably include effective amounts of the lubricity enhancing component and are exposed to plasma to facilitate passage of the IOL from the loading portion into the hollow tube and from the hollow tube into the eye. In addition, it is often more convenient to treat both the hollow tube and loading portion, which together preferably are a single, integrally formed unit, with the lubricity enhancing component and plasma, rather than treating only the hollow tube.

The loading portion preferably is sized and adapted to receive an IOL, for example, in an unfolded state, and to hold the IOL in a folded state. The loading portion can be structured to at least facilitate the folding of the IOL from the unfolded state to a folded state. The hollow tube includes an interior wall which defines a hollow space preferably sized to receive the IOL in a folded state from the loading portion and to pass the folded IOL to an open outlet through which the IOL is passed into an eye.

Methods for producing apparatus for inserting an IOL through a small incision in the eye are provided and are included within the scope of the present invention. These methods have, in general, been discussed above, and comprise exposing a hollow tube to plasma and providing an effective amount of a lubricity enhancing component physically secured to said hollow tube and concentrated at or near the interior wall of the hollow tube. More specifically, the plasma employed is preferably a sub-atmospheric pressure plasma, more preferably a sub-atmospheric pressure, oxygen-containing plasma, although other plasmas are suitable.

As used herein, the term "concentrated" means that the lubricity enhancing component is located in a higher concentration at or near one or more portions, for example, the surfaces, of an article than at one or more other portions, for example, the interior, of the article. This includes the situation in which the lubricity enhancing component is located as a coating on the interior surface of the hollow tube and is not present in the hollow tube itself. Also included is a situation in which the hollow tube includes a concentration of lubricity enhancing component throughout with a locally higher concentration present at or near the interior surface of the hollow tube.

In one embodiment, the lubricity enhancing component is physically secured or bonded to the hollow tube prior to the exposing step. In a particularly useful embodiment, the providing step includes subjecting the hollow tube having an amount of lubricity enhancing component spaced apart from the interior wall to conditions effective to cause this amount of lubricity enhancing component to form at least a portion of the effective amount of the lubricity enhancing component at or near the interior wall. For example, the hollow tube can be subjected to elevated temperatures for substantial periods of time, such as on the order of about 6 hours or about 12 hours to about 100 hours or more, to cause the lubricity enhancing component to move toward the surface. This "blooming" action is very effective in providing the desired amount of lubricity enhancing component concentrated at or near the interior wall of the hollow tube.

In addition, the loading portion can be formed by comparable exposing and providing steps.

Methods for inserting an IOL into an eye are also provided and are included within the scope of the present invention. In one embodiment, such methods comprise placing an outlet or distal end opening of the hollow tube of the present apparatus in or in proximity to an incision in an eye, and passing an IOL from the hollow tube through the outlet or opening into the eye.

These and other aspects of the present invention will become apparent in the following detailed description and claims, particularly when considered in conjunction with the accompanying drawings in which like parts bear like reference numerals.

BRIEF DESCRIPTION OF THE DRAWINGS

FIG. 1 is a front side view, in perspective, of an apparatus in accordance with the present invention with the load chamber in the open position.

FIG. 2 is a fragmentary, schematic illustration of a small portion of the apparatus shown in FIG. 1.

FIG. 2A is a fragmentary, schematic illustration of a small portion of a modified embodiment of the apparatus shown in FIG. 1 which includes a coating.

FIG. 3 is a side view, in perspective, of the apparatus shown in FIG. 2 with the load chamber in the closed position.

FIG. 4 is a front side view, in perspective, of the apparatus shown in FIG. 3 loaded into a hand piece.

FIG. 5 is a side view, partly in cross-section, taken generally along line 5—5 of FIG. 4.

FIG. 6 is a somewhat schematic illustration showing the apparatus shown in FIG. 4, with the hand piece partially in cross-section, being used to insert an IOL into an eye.

DETAILED DESCRIPTION OF THE DRAWINGS

FIG. 1 illustrates an IOL inserter, shown generally at 10, including a load chamber 12 and an injection tube 14. The IOL inserter 10 is made of polypropylene to which has been physically added an amount, for example, in the range of about 0.1% to about 5% by weight of the inserter, of a lubricity enhancing component, for example, an oleophilic component such as glycerol monostearate or a hydrophilic component such as polyvinylpyrrolidone.

The lubricity enhancing component is physically admixed with the other material from which the inserter 10 is made, preferably prior to forming the inserter. In a particularly useful embodiment, the lubricity enhancing component is combined with the other material, for example, a polymeric material, such as polypropylene, while the material is in the molten or fluid state. The lubricity enhancing component can be blended in this material so that it is substantially uniformly distributed throughout the material. The material is then placed in a mold or similar device suitable for forming the inserter 10. After the inserter 10 is formed, the lubricity enhancing component remains substantially uniformly distributed throughout the inserter.

Once the inserter 10 is formed, it is processed to provide enhance lubricity. The inserter 10 is exposed to an effective plasma. For example, the inserter 10 can be placed in a chamber containing a plasma. The plasma may have its origin for any of a variety of materials, preferably gases, in particular gases such as oxygen, helium, nitrogen, argon and mixtures thereof. More preferably an oxygen-containing plasma is used.

In accordance with one embodiment of the present invention, radio frequency, inductively-coupled plasma is produced in a plasma chamber by charging the chamber with gas, e.g., oxygen, preferably at a sub-atmospheric pressure such as about 0.01 torr (mm Hg) or greater, more preferably at a pressure in the range of about 0.01 torr to about 0.3 torr or about 0.5 torr or about 1.0 torr. The preferred output power is in the range of about 10 watts to about 600 watts.

The inserter 10 is preferably exposed to the plasma for a period of time in the range of about 15 seconds to about 120 minutes and more preferably about 30 seconds to about 100 minutes. However, the specific gas, exposure time, power and/or other parameters may be varied depending upon the equipment and the particular inserter and inserter components involved, and can be readily optimized based on the disclosure herein using routine experimentation.

Although the present invention is not limited to any particular mechanism, and without limiting the present invention to any particular theory of operation, the present methodology is believed to cause a modification or alteration, for example, a physical and/or chemical modification or alteration, of the exposed regions of the inserter, which, in turn, results in enhanced lubricity.

In addition, inserter 10 is subjected to conditions effective to form an interior wall on or near which is present a higher concentration of lubricity enhancing component relative to the lubricity enhancing component concentration present in the interior of the inserter. A particularly useful embodiment involves subjecting the inserter to an elevated temperature for a time effective to cause the lubricity enhancing component to migrate toward the surfaces, for example, the interior surface, of the inserter. A common name for this phenomenon is "blooming". Preferably, the inserter 10 is subjected to elevated temperatures of at least about 35° C., more preferably in the range of about 40° C. or about 45° C. to about 100° C. or about 120° C., for a time in the range of about 6 hours to about 150 hours and more preferably in the range of about 8 hours to about 120 hours.

Again, without wishing to limit the invention to any particular theory of operation, it is believed that this "blooming" step causes a portion of the lubricity enhancing component present in the inserter 10 to be located at or near the interior surface of the inserter. However, it is also believed that this lubricity enhancing component at or near the interior surface of the inserter is physically, rather than covalent chemically, secured or bound to the inserter. However, it has been found that both the "blooming" step and the plasma exposing step, in combination, are very advantageous to provide enhanced lubricity to the inserter. In other words, an inserter which has only been subjected to the "blooming" step or which has only been subjected to the plasma exposing step provides substantially less advantageous results than if the inserter is subjected to both the "blooming" step and the plasma exposing step.

Alternately, the inserter 10 can be formed and then treated with a lubricity enhancing component, preferably selected from oleophilic components, hydrophilic components and mixtures thereof. For example, the inserter 10 can be immersed in or sprayed with a lubricity enhancing component or a medium, such as an aqueous medium, including a lubricity enhancing component one or more times so as to provide a surface coating, preferably a substantially uniform surface coating of the lubricity enhancing component, for example, on the interior surfaces or walls of the inserter. The inserter 10 is exposed to a plasma, as discussed elsewhere herein, either prior to or after, preferably prior to, providing a surface coating of lubricity enhancing component.

In any event, the lubricity enhancing component is present in an amount effective, in combination with the plasma exposing step, to enhance or facilitate the passage of the IOL through the inserter 10 into the eye. It should be noted that the lubricity enhancing component need not be substantially present within the inserter 10 as discrete particles. However, substantially no covalent chemical bonds exist between the lubricity enhancing component and the other material making up the inserter 10.

The lubricity enhancing components useful in the present invention may be selected from suitable components which function as described herein. Although the lubricity enhancing component is preferably inhibited from passing into the eye during use of the present apparatus, lubricity enhancing components which are substantially non-irritating to ocular tissue and/or are substantially biocompatable with ocular tissue are particularly useful in accordance with the present invention. The lubricity enhancing component is present in an amount effective to enhance the lubricity of the interior wall of the hollow tube defining a hollow space through which the IOL passes in being inserted into the eye. Such lubricity enhancing components are preferably effective to provide such enhanced lubricity for relatively long periods of time, for example, for at least about 1 month or at least about 3 months or at least about 6 months, so that the IOL inserter has a relatively long shelf life and can be used after being packaged and stored for such relatively long periods of time and still obtain the substantial enhanced lubricity benefits.

The physical securing or bonding of the lubricity enhancing component to the IOL inserter preferably is effective to reduce the amount of this component which is passed into the eye as the IOL is inserted into the eye. In other words, it is preferred that such physical securing or bonding is effective to inhibit the lubricity enhancing component from passing into the eye as the IOL is inserted into the eye. Thus, the present invention conveniently provides for enhanced lubricity and ease of inserting an IOL into an eye while, at the same time, reducing the amount of lubricity enhancing component in the eye and eliminating the need for any covalent chemical reaction or reactions between the material of the inserter and the lubricity enhancing component.

Particularly useful oleophilic components include, but are not limited to, those selected from carboxylic acids having about 10 to about 30, carbon atoms per molecule, glycerol esters of such carboxylic acids, such as glycerol monostearate, glycerol monopalmitate, glycerol monooleate and the like, and mixtures thereof.

Particularly useful hydrophilic lubricity enhancing components include, but are not limited to, those selected from polyethylene glycol, polyvinylpyrrolidone, poly (N-vinyl lactams), polyacrylic acid, polyethylene oxide, polypropylene oxide, polyvinyl pyridine, polyvinyl alcohol, polysaccharides, carboxy methyl cellulose, hydroxy alkyl celluloses, such as hydroxypropylmethyl cellulose and the like, polymethacrylic acid, polyacrylamide, polypeptides, poly sodium styrene sulfonate, polyhydroxyethyl methacrylate, heparin and the like and mixtures thereof. If a hydrophilic lubricity enhancing component is employed, it is preferred that the IOL inserter be immersed or otherwise contacted with water, for example, a saline solution, to hydrate the hydrophilic component. Such hydration is effective to facilitate the lubricity enhancing characteristics of the hydrophilic component.

In addition to the physically secured or bonded lubricity enhancing component, the inserter 10 may also include a covalently bonded lubricity enhancing component, for example, as a coating on the exposed surfaces, such as the interior surfaces of the inserter. Such additional covalently bonded lubricity enhancing component is effective to further enhance the lubricity of inserter 10. The covalently bonded lubricity enhancing component can be included in or on the inserter 10 in any suitable manner.

FIGS. 1 and 3 to 6 illustrate the use of IOL inserter 10 including an effective amount of physically secured or bonded lubricity enhancing component 19 (FIG. 2) or 20 (FIG. 2A) concentrated at or near the interior surfaces thereof.

The body of IOL inserter 10 is an integrally formed, for example, molded, unit made primarily of propropylene. Load chamber 12 includes a first member 16 and a second member 18 which are secured or joined together and are hingeably moveable relative to each other along line 21, which is parallel to the longitudinal axis 30 of inserter 10.

Injection tube 14 includes a proximal end portion 22, a distal end portion 24 and an open distal end 26. A reinforcing collar 28 is coincidental with the proximal end portion 22 of injection tube 14.

Open distal end 26 is beveled at an angle of about 45° relative to the longitudinal axis 30 of the inserter 10.

Injection tube 14 includes a through slot 32 which extends from the open distal end 26 distally and terminates prior to the proximal end portion 22 of injection tube 14. Through slot 32 is elongated in a direction parallel to the longitudinal axis 30 of inserter 10.

As shown in FIG. 1, inserter 10 is in the opened position. In contrast, in FIG. 3, inserter 10 is shown in the closed position. In the closed position, the load chamber 12 includes a top 32 which is a combination of top surfaces 34 and 36 of first wing 38 and second wing 40, respectively, of first member 16 and second member 18, respectively. First and second wings 38 and 40 are effective for a human user of inserter 10 to hold and manipulate the inserter 10 while using it, as described hereinafter.

Inserter 10 is described in more detail with reference to FIG. 4, which shows the inserter in combination with hand piece 50. When used in combination with hand piece 50, the load chamber 12 of inserter 10 is in the closed position, as shown in FIG. 4. With the load chamber 12 in the closed position, and top 32 being the uppermost portion of the load chamber, open distal end 26 of injection tube 14 is beveled at an angle of 45° relative to the longitudinal axis 30 of the inserter 10 so that the open distal end is generally right facing (when the inserter is viewed from above). In addition, through slot 32 intersects the open distal end 26 at the proximal most portion of the open distal end, as shown in FIGS. 1, 3 and 5.

Referring to FIG. 5, with load chamber 12 in the closed position, the load chamber includes an interior wall 51 which defines a first lumen 52 that is elongated in a direction parallel to the longitudinal axis 30 of inserter 10. Injection tube 14 includes a tapering interior wall 53 which defines a distally tapering second lumen 54. The average cross-sectional area of second lumen 54 transverse to the longitudinal axis 30 is smaller than or reduced relative to the average cross-sectional area of the first lumen 52.

The first lumen 52 is aligned with the second lumen 54 so that a folded IOL in the first lumen can be passed directly from the first lumen into the second lumen. The taper of proximal portion 58 of second lumen 54 is more severe than the slight taper which exists in the distal portion 60 of the second lumen. The more severe taper in the proximal portion 58 is effective to further fold the IOL as the IOL is passed into the second lumen 54. This further folding is advantageous because the further folded IOL can be inserted into the eye through a smaller incision. The enhanced lubricity resulting from the oleophilic component 19 facilitates this further folding so that a reduced amount of force is required to further fold the IOL and/or the degree of further holding of the IOL can be increased so that ultimately, the IOL can be inserted through an even smaller incision. The oleophilic component 19 also advantageously reduces the risk of tearing and/or otherwise damaging the IOL as the IOL is passed through the first lumen 52 and second lumen 54.

With reference to FIG. 4, inserter 10 is shown in combination with hand piece 70 and push rod member 72. Hand piece 70 includes a relatively large, elongated first through opening 74 and a relatively small, elongated second through opening 76. Hand piece 70 includes a through bore 78 which extends from the proximal end 80 to the distal end 82 of the hand piece. The proximal end portion 84 of hand piece 70 includes threads 86 which are adapted to engage and mate with threads 88 of the proximal segment 90 of push rod member 72. Rod element 92 of push rod member 72 is adapted to pass through bore 78, first lumen 52, second lumen 54 and out of open distal end 26. Hand piece 70 and push rod member 72 are made of metal, such as surgical grade stainless steel or the like metals.

Inserter 10 is operated and functions as follows. When it is desired to load an IOL into inserter 10, the inserter is placed, for example, manually placed, in a configuration as shown in FIG. 3. With load chamber 12 in the opened position, an IOL, such as is shown generally at 100, is placed, for example, using forceps, in between first and second members 16 and 18. This placement is such that the anterior face 102 of optic 104 faces upwardly, as shown in FIG. 1. The optic 104 is made of a silicone polymeric material. The filament haptics 106 and 108 of IOL 100 are located as shown in FIG. 1, so that the fixation members are located generally parallel to, rather than transverse to, the longitudinal axis 30.

With IOL 100 placed as shown in FIG. 1, first and second members 16 and 18 are hingeably moved relative to each other, for example, by manually bringing first and second wings 38 and 40 together, to place the load chamber 12 in the closed position, as shown in FIG. 3. With load chamber 12 in the closed position, IOL 100 is in a folded state, that is optic 104 is folded. The relative movement of first and second members 16 and 18 to move the load chamber from the open position to the closed position is effective to fold the lens. The folded IOL 100 is now located in the first lumen 52. For clarity sake, the folded IOL is not shown in any of FIGS. 3, 4, 5 or 6.

With the inserter 10 configured as shown in FIG. 3 and folded IOL 100 located in first lumen 52, the inserter 10 is placed in association with hand piece 70, as shown in FIG. 4. In this configuration, the distal end portion 24 of injection tube 14 extends distally beyond the distal end 82 of hand piece 70. As shown in FIG. 5, the distal portion 85 of hand piece 70 includes an inner wall 87 which is configured to receive reinforcing collar 28 in abutting relation.

With inserter 10 so placed relative to hand piece 70, push rod member 72 is placed into the through bore 78 of the hand piece starting at the proximal end 80. As threads 88 come in contact with and engage threads 86, the push rod member 72 is rotated, as shown in FIG. 6, so as to thread the push rod member onto the proximal end portion 84 of hand piece 70. By gradually moving push rod element 92 through bore 78 of hand piece 70, the folded IOL 100 is urged to move from first lumen 52 into second lumen 56, through open distal end 26 and into the eye.

Referring now to FIG. 6, the IOL 100 is to be placed in eye 120 into an area formerly occupied by the natural lens of the eye. FIG. 6 shows the sclera 122 having an incision through which the distal end portion 24 of injection tube 14 is passed. Alternately, the incision can be made through the cornea. Distal end portion 24 has a sufficiently small cross-section to pass into the eye 122 through a 3.0 mm incision in the sclera 122.

The injection tube 14 is manipulated within eye 122 until it is positioned so that IOL 100 can be properly positioned in eye 122, that is in the anterior chamber, the posterior chamber, the capsular bag 124 or in the sulcus, after being released. Thus, the surgeon is able to controllably position the distal end portion 24 of injection tube 14, with IOL 100 in the first lumen 52 of load chamber 12. Once distal end portion 24 is so positioned, the rod element 92 is urged distally, by rotating (threading) push rod member 72 onto hand piece 70, to pass the IOL 100 into and through the second lumen 54, through the open distal end 26 of injection tube 14 and into the eye 120. The anterior face 102 of IOL 100 faces generally forwardly in the eye 120 as the IOL is released from the inserter 10. In other words, the IOL 100 passes through first lumen 52, second lumen 54 and open distal end 26 and into eye 120 without flipping or otherwise becoming mispositioned. Only a relatively small amount of, if any, post-insertion re-positioning is needed to properly position IOL 100 in eye 120.

After the IOL 100 has been inserted into the eye, the rod element 92 is moved proximally into the injection tube 14 and the distal end portion 24 of the injection tube is removed from the eye. If needed, the IOL 100 can be re-positioned in the eye by a small, bent needle or similar tool inserted into the same incision.

Once the IOL 100 is properly positioned in eye 120 and inserter 10 is withdrawn from the eye, the incision in the sclera may be mended, for example, using conventional techniques. After use, inserter 10 is preferably disposed of. Hand piece 70 and push rod member 72 can be reused, after sterilization/disinfection.

The following non-limiting examples illustrate certain aspects of the present invention.

EXAMPLES

A series of IOL inserters, similar in configuration to inserter 10, were provided and tested.

These inserters were as follows:

INSERTER A: molded from polypropylene including 0.25% by weight of glycerol monostearate distributed substantially uniformly throughout. Inserter A was subjected to no plasma processing and no blooming processing.

INSERTER B: molded from polypropylene including 0.25% by weight of glycerol monostearate distributed substantially uniformly throughout. Inserter B was subjected to plasma processing, but no blooming processing.

INSERTER C: molded from polypropylene including 0.25% by weight of glycerol monostearate distributed uniformly throughout. Inserter C was subjected to no plasma processing and to four (4) days of blooming processing.

INSERTER D: molded from polypropylene including 0.25% by weight of glycerol monostearate distributed uniformly throughout. Inserter D was subjected to plasma processing and one (1) day of blooming processing.

INSERTER E: same as Inserter D except subjected to plasma processing and to two (2) days of blooming processing.

INSERTER F: same as Inserter D except subjected to plasma processing and to three (3) days of blooming processing.

INSERTER G: same as Inserter D except subjected to plasma processing and to four (4) days of blooming processing.

The plasma processing referred to above was performed using a PS-0150 plasma unit at 25 watts power. The plasma gas included oxygen at a flow rate of 30–50 cc/min. The plasma pressure was 0.05 to 0.10 torr and the time of plasma exposure was 90 minutes.

The blooming processing referred to above was performed by subjecting the inserter to a temperature of 50° C. in air for the designated period of time. In all cases in which plasma processing and blooming processing both occurred, the plasma processing preceded the blooming processing.

A series of tests were run to evaluate the lubricity of the inserters provided.

In each of the tests, the inserter rod was equipped with a soft distal tip molded from a silicone polymeric elastomer made from a formulation sold by NuSil Technology under the trademark Nusil 4516. These tips were sized and adapted to be received and held or trapped in the fold of an IOL being passed through an inserter.

Except for the presence of the tip and the use of the inserters noted above, the system used in this testing was the IOL injector system sold by Allergan, Inc. under the trademark PIC 1. The lenses used in the testing had varying optical powers and included optics made of elastomeric silicone-based polymeric materials. Specifically the IOLs were those sold by Allergan, Inc. under the trademarks SI-30 and SI-40.

The test procedure used was as follows. The IOL was loaded into the loading chamber and the inserter was placed into the hand piece. An amount of commercially available sodium hyaluronate-containing aqueous solution approximately equal to the volume of the IOL optic was dispensed into the loading chamber. In certain tests the IOL was immediately advanced through the entire forward tube and then out the distal port. In other tests, the IOL was allowed to dwell in the loading chamber (Stage 1) a period of time specified and then was advanced into the forward tube. The IOL was allowed to dwell in the forward tube (Stage 2) for a specified period of time before being released out the distal port. After the IOL was released, the rod and tip were cleaned with water and the tip was reused up to five (5) times.

Results of these tests were as follows:

| INSERTER | IOL STYLE | POWER, DIOPTERS | DWELL TIME[1] STAGE 1/STAGE 2 | FORCE REQUIRED | IOL RELEASE |
|---|---|---|---|---|---|
| A | S1–40 | 16.5 TO 25 | 0–4/0–2 MIN. | | LENSES WOULD NOT MOVE |
| B | S1–40 | 16.5 TO 25 | 0–4/0–2 MIN. | | LENSES WOULD NOT MOVE |
| C | S1–40 | 16.5 TO 25 | 0–5/0–8 MIN. | | LENSES WOULD NOT MOVE |
| D | S1–30 | 21.5 | 0 MIN. | MODERATE | VERY WELL CONTROLLED |
| D | S1–40 | 21.5 | 5/2–8 MIN. | FAIL | ROD BYPASSED THE LENS |
| E | S1–40 | 16.5 | 0–4/0–2 MIN. | MODERATE | VERY WELL CONTROLLED |
| E | S1–40 | 20.0 | 0–4/0–2 MIN. | MODERATE TO HIGH | VERY WELL CONTROLLED |
| E | S1–40 | 24.5 | 0–4/0–2 MIN. | LOW TO MODERATE | VERY WELL CONTROLLED |
| F | S1–40 | 16.5 | 0–4/0–2 MIN. | MODERATE | VERY WELL CONTROLLED |
| F | S1–40 | 20.5 | 0–4/0–2 MIN. | MODERATE | VERY WELL CONTROLLED |
| F | S1–40 | 25.0 | 0–4/0–2 MIN. | MODERATE | VERY WELL CONTROLLED |
| G | S1–40 | 15.5 | 0–4/0–2 MIN. | LOW TO MODERATE | VERY WELL CONTROLLED |
| G | S1–40 | 20.5 | 0–4/0–2 MIN. | MODERATE | VERY WELL CONTROLLED |
| G | S1–40 | 24.5 | 0–4/0–2 MIN. | MODERATE | VERY WELL CONTROLLED |

[1]More than one test was run for many of the inserter/IOL style/power combinations. The dwell time was often varied from test to test. Thus, the dwell times are shown in terms of ranges of time.

These results indicate that Inserter A, even though it included 0.25% by weight of glycerol monostearate, is ineffective to insert IOLs in the test conducted. In addition, Inserters B and C—which were subjected to either plasma processing or blooming processing—but not both—are ineffective to insert IOLs in the tests conducted. Further, Inserter D—which was subjected to plasma processing and a limited amount of blooming processing—is somewhat effective to insert IOLs in the tests conducted. However, Inserters E, F and G which were subject to both plasma processing and substantial blooming processing are effective to insert IOLs in the tests conducted.

The IOL inserter cartridges in accordance with the present invention have an enhanced ability to pass IOLs for insertion into the eye. The enhanced lubricity of these cartridges, resulting from physically admixed or combined oleophilic components, allows reduced force to be used to pass an IOL, relative to the force needed to pass an IOL through a cartridge without the oleophilic component. This reduced force requirement results in advantageously reducing the risk of harming the cartridge (inserter) and/or the IOL by passing an IOL through the cartridge. Thus, the relatively straightforward and uncomplicated physically admixing or combining of an oleophilic component into an IOL inserter provides a substantial and outstanding combination of benefits.

Comparable results are obtained using similar inserters and methodologies in which the glycerol monostearate is replaced by an effective amount of polyvinylpyrrolidone, a hydrophilic lubricity enhancing component.

A second series of IOL inserters, similar in configuration to inserter 10, were provided and tested.

These inserters were molded from polypropylene including 0.25% by weight of glycerol monostearate distributed substantially uniformly throughout. These inserters were subjected to plasma processing using a PS-0150 plasma unit at 500 watts power. The plasma gas included oxygen at a flow rate of 30–50 cc/min. The plasma pressure was 0.05 to 0.10 torr and the time of plasma exposure was 2 minutes. Immediately after plasma processing, the inserters were coated with an aqueous solution containing 1% by weight of hydroxypropylmethylcellulose (HPMC). The inserters were dried at 70° C. for 15 minutes.

The plasma processing, coating and drying steps were repeated except that the plasma processing occurred for a period of 1 minute. The inserters were then sterilized using ethylene oxide.

A series of tests, using the test procedure outlined previously, were run to evaluate the lubricity of the inserters provided.

Results of these tests were as follows:

| INSERTER | IOL STYLE | POWER, DIOPTERS | DWELL TIME STAGE 1/STAGE 2 | FORCE REQUIRED | IOL RELEASE |
|---|---|---|---|---|---|
| 1 | S1–30 | 12 | 0 MIN. | MODERATE | CONTROLLED |
| 2 | S1–40 | 12 | 5/2 MIN. | LOW/MODERATE | VERY WELL CONTROLLED |
| 3 | S1–40 | 12 | 5/5 MIN. | LOW/MODERATE | VERY WELL CONTROLLED |
| 4 | S1–40 | 12 | 5/8 MIN. | LOW/MODERATE | CONTROLLED |
| 5 | S1–40 | 12 | 0/5 MIN. | LOW/MODERATE | VERY WELL CONTROLLED |
| 6 | S1–30 | 12 | 0 MIN. | MODERATE | CONTROLLED |
| 7 | S1–40 | 20 | 5/2 MIN. | LOW/MODERATE | CONTROLLED |
| 8 | S1–40 | 20 | 5/5 MIN. | LOW/MODERATE | CONTROLLED |
| 9 | S1–40 | 20 | 5/8 MIN. | LOW/MODERATE | CONTROLLED |
| 10 | S1–40 | 20 | 0/5 MIN. | LOW | VERY WELL CONTROLLED |
| 11 | S1–30 | 24 | 0 MIN. | MODERATE | VERY WELL CONTROLLED |
| 12 | S1–40 | 25 | 5/2 MIN. | LOW | CONTROLLED |
| 13 | S1–40 | 25 | 5/5 MIN. | LOW/MODERATE | VERY WELL CONTROLLED |
| 14 | S1–40 | 25 | 5/8 MIN. | LOW/MODERATE | VERY WELL CONTROLLED |
| 15 | S1–40 | 25 | 0/5 MIN. | LOW/MODERATE | CONTROLLED |

These results demonstrate that the inserters processed with plasma and HPMC have sufficient lubricity to facilitate the passage of an IOL through the inserter.

Comparable results are obtained with inserters being subjected to plasma processing, as described with regard to the second series of tests, coating with an aqueous solution containing 2% to 3% by weight of HPMC and drying at 70° C. for 15 minutes on a one-time basis (as opposed to the repeated plasma processing, coating and drying steps noted above).

While this invention has been described with respect of various specific examples and embodiments, it is to be understood that the invention is not limited thereto and that it can be variously practiced within the scope of the following claims.

What is claimed is:

1. A method for making an apparatus for inserting an intraocular lens through a small incision into an eye, said method comprising:

exposing a hollow tube including a material and having an interior wall defining a hollow space through which an intraocular lens is passed and an outlet through which the intraocular lens is passed from said hollow space into an eye to a plasma effective to provide a plasma-exposed interior wall having an enhanced ability to physically secure a lubricity enhancing component relative to a substantially identical interior wall which is not plasma exposed; and providing an amount of a lubricity enhancing component physically secured, other than by covalent bonding, to said hollow tube and concentrated at or near said interior wall, said exposing step and said providing step together being effective to facilitate passing an intraocular lens through said hollow space relative to passing an identical intraocular lens through the hollow space of a substantially identical hollow tube which has not been subjected to said exposing step and said providing step.

2. The method of claim 1 wherein said lubricity enhancing component is physically admixed with said material prior to said exposing step.

3. The method of claim 1 wherein said exposing step occurs at sub-atmospheric pressure in the presence of oxygen.

4. The method of claim 1 wherein said material is a polymeric material.

5. The method of claim 1 wherein said lubricity enhancing component is selected from the group consisting of oleophilic components, hydrophilic components and mixtures thereof.

6. The method of claim 1 wherein said lubricity enhancing component is an oleophilic component.

7. The method of claim 1 wherein said providing step includes subjecting said hollow tube having an amount of lubricity enhancing component spaced apart from said interior wall to conditions effective to concentrate of said lubricity enhancing component at or near said interior wall.

8. The method of claim 7 wherein said lubricity enhancing component is an oleophilic component, said conditions include a temperature of at least about 40° C., and said lubricity enhancing component is substantially uniformly distributed throughout said hollow tube prior to said subjecting.

9. The method of claim 7 wherein said exposing step occurs prior to said subjecting.

10. The method of claim 1 which further comprises:

exposing a loading zone coupled to said hollow tube and including a material and having an internal wall defining a chamber sized to receive an intraocular lens for passage into said hollow space to said plasma; and providing an amount of said lubricity enhancing component physically secured, other than by covalent bonding, to said loading zone and concentrated at or near said internal wall of said loading zone, said exposing step and said providing step together being effective to facilitate the passage of an intraocular lens into said hollow space relative to passing an identical intraocular lens into the hollow space from a substantially identical loading zone which has not been subjected to said exposing step and said providing step.

11. A method for making an apparatus for inserting an intraocular lens through a small incision into an eye, the method comprising:

provocative a hollow tube including a material and an amount of lubricity enhancing component physically admixed throughout said material, said hollow tube having an interior wall defining a hollow space through which an intraocular lens is passed and an outlet through which the intraocular lens is passed from said hollow space into an eye;

exposing said hollow tube to plasma effective to provide a plasma-exposed interior wall having an enhanced ability to physically secure said lubricity enhancing component relative to a substantially identical interior wall which is not plasma exposed; and subjecting said hollow tube to conditions effective to concentrate said lubricity enhancing component at or near said interior wall.

12. The method of claim 11 wherein said exposing step and said subjecting step together are effective to facilitate passing an intraocular lens through said hollow space relative to passing an identical intraocular lens through the hollow space of a substantially identical hollow tube which has not been subjected to said exposing step and said subjecting step.

13. The method of claim 11 wherein said exposing step precedes said subjecting step.

14. The method of claim 11 wherein said lubricity enhancing component is physically admixed with said material prior to said exposing step.

15. The method of claim 11 wherein said exposing step occurs at sub-atmospheric pressure in the presence of oxygen.

16. The method of claim 11 wherein said material is a polymeric material.

17. The method of claim 11 wherein said lubricity enhancing component is selected from the group consisting of oleophilic components, hydrophilic components and mixtures thereof.

18. The method of claim 11 wherein said lubricity enhancing component is an oleophilic component.

19. The method of claim 11 wherein said lubricity enhancing component is an oleophilic component, said conditions include a temperature of at least about 40° C., and said lubricity enhancing component is substantially uniformly distributed throughout said hollow tube prior to said subjecting.

* * * * *

UNITED STATES PATENT AND TRADEMARK OFFICE
CERTIFICATE OF CORRECTION

PATENT NO. : 5,942,277  Page 1 of 1
DATED : August 24, 1999
INVENTOR(S) : Makker et al.

It is certified that error appears in the above-identified patent and that said Letters Patent is hereby corrected as shown below:

<u>Title page,</u>
Item [57], ABSTRACT, delete in its entirety and insert in place thereof:
-- Apparatus for inserting intraocular lenses (IOLs) into eyes include a hollow tube including a material and having an interior wall defining a hollow space through which an IOL is passed and an outlet through which the IOL is passed from the hollow space into an eye, and a lubricity enhancing component physically secured to said hollow tube and concentrated at or near the interior wall in an amount effective to facilitate the passage of the IOL through the hollow space. --

Signed and Sealed this

Seventeenth Day of February, 2004

JON W. DUDAS
*Acting Director of the United States Patent and Trademark Office*